United States Patent [19]

Mukaida et al.

[11] Patent Number: 5,986,166
[45] Date of Patent: Nov. 16, 1999

[54] ABSORBENT PRODUCT INCLUDING ABSORBENT LAYER TREATED WITH SURFACE ACTIVE AGENT

[75] Inventors: Shingo Mukaida, Higashiyama-ku; Kazuhiko Iguchi, Kyoto-fu; Kenji Tanaka, Shiga-ken, all of Japan

[73] Assignee: Sanyo Chemcial Industries, Ltd., Kyoto, Japan

[21] Appl. No.: 08/866,578

[22] Filed: May 30, 1997

Related U.S. Application Data

[62] Division of application No. 08/590,586, Jan. 24, 1996, Pat. No. 5,676,660.

[30] Foreign Application Priority Data

Feb. 8, 1995 [JP] Japan ................................. 7-044752
Feb. 8, 1995 [JP] Japan ................................. 7-044753

[51] Int. Cl.⁶ ................................................. A61F 13/15
[52] U.S. Cl. .......................... 604/368; 604/372; 604/375
[58] Field of Search ................................. 604/367, 368, 604/369, 372, 375, 378

[56] References Cited

U.S. PATENT DOCUMENTS

| | | | |
|---|---|---|---|
| 3,693,622 | 9/1972 | Jones, Sr. ............................ | 128/290 R |
| 3,920,020 | 11/1975 | Kraskin . | |
| 4,096,311 | 6/1978 | Pietreniak ............................... | 604/365 |
| 4,286,082 | 8/1981 | Tsubakimoto et al. ................. | 526/240 |
| 4,356,229 | 10/1982 | Brodnyan et al. ....................... | 428/288 |
| 4,377,615 | 3/1983 | Suzuki et al. ............................ | 604/365 |
| 4,408,996 | 10/1983 | Baldwin . | |
| 4,535,098 | 8/1985 | Evani et al. ............................ | 521/149 |
| 4,804,378 | 2/1989 | Shiba et al. . | |
| 5,079,081 | 1/1992 | Lal . | |
| 5,281,207 | 1/1994 | Chmielewski et al. . | |
| 5,360,420 | 11/1994 | Cook et al. . | |
| 5,429,590 | 7/1995 | Saito et al. . | |
| 5,508,381 | 4/1996 | Jang et al. . | |
| 5,514,122 | 5/1996 | Morris et al. ........................... | 604/387 |

FOREIGN PATENT DOCUMENTS

| | | |
|---|---|---|
| 58-60068 | 4/1983 | Japan . |
| 1-148879 | 6/1989 | Japan . |
| 2-169774 | 6/1990 | Japan . |

*Primary Examiner*—Robert A. Clarke
*Assistant Examiner*—Ki Yong O
*Attorney, Agent, or Firm*—Merchant, Gould, Smith, Edell, Welter & Schmidt, P.A.

[57] ABSTRACT

An absorbent product comprising a liquid permeable surface sheet, a liquid nonpermeable back sheet and an absorbent layer located therebetween, wherein the absorbent layer comprises a water nonswellable synthetic fiber (a) and optionally cellulose fiber (b), and a water-absorbent resin (c), with the weight ratio of (a):(b) being (100 to 20):(0 to 80) and the percentage content of (c) based on the weight sum of (a), (b) and (c) is 25 to 75 weight %. The absorbent layer is treated with polyoxyalkylene-modified silicone surface active agent (d1) and/or a nonsilicone surface active agent having HLB of 8 to 14 (d2). Absorbent products of the present invention exhibit excellent shape retention in the moist state and good permeability and diffusibility for the absorbed liquid. Accordingly, they provide excellent surface dryness, reduced leakage and thus can be comfortably used for a long time and effectively applied to disposable diapers, sanitary napkins and incontinence pads.

6 Claims, No Drawings

ABSORBENT PRODUCT INCLUDING ABSORBENT LAYER TREATED WITH SURFACE ACTIVE AGENT

This is a Divisional of application Ser. No. 08/590,586, now U.S. Pat. No. 5,676,660 filed Jan. 24, 1996, which application is incorporated herein reference.

BACKGROUND OF THE INVENTION

1. Field of the Invention

The present invention relates to disposable absorbent products such as disposable diapers, sanitary napkins and incontinence pads. More specifically, it relates to absorbent products exhibiting excellent permeability and diffusibility of the absorbed liquid in the absorbent layer without leakage, thereby providing good dryness and comfort to the user.

2. Description of the Prior Art

Hitherto, various proposals have been advocated for absorbent products' properties aimed at improving the absorption rate of urine or blood, improving the dryness after absorption, or reducing leakage.

Most of such proposals relate to improvement of the liquid permeable surface sheet or surface nonwoven fabric (as disclosed in the official gazette notice for JP-A-58-60068, the official gazette notice for JP-A-1-148879 and the official gazette notice for JP-A-2-169774), use of water-absorbent resins having a specific performance or property, disposition of an absorbent resin in the absorbent layer, use of a hydrophilic diffusion layer comprising a nonwoven fabric or a water-absorbent paper, and an embossing method for the absorbent layer. Thus few improvements concerning the absorbent layer itself containing an absorbent resin have been proposed so far. This is because conventional disposable diapers have an absorbent layer made of materials with a high hydrophilic property, such as fluff pulp, water absorbent paper and water absorbent resin.

These days, with the property improvement of absorbent products such as disposable diapers and sanitary napkins, such products tend to be used over a long time. Further, as to disposable diapers, as they become thinner, the ratio of water absorbent resin/fiber substrate therein tends to become greater. On the other hand, satisfactory shape retention or unity of the water absorbent resin/fiber substrate can not be obtained with an absorbent layer comprising a water-absorbent resin and a conventional cellulose fiber such as fluff pulp and water absorbent paper, regardless of the application of the water-absorbent resin, namely, whether in a method of sandwiching between pulp layers or water absorbent papers, or in a method of mixing with pulp. That is, hydrophilic cellulose fibers that absorb and retain liquid such as urine and blood by physical capillary action have problems such as susceptibility to deformation by an external force such as the wearer's movement during a period of water absorption or after water absorption to ruin the unity of the water absorbent resin/fiber substrate, which lead to leakage and deterioration of dryness.

Proposals to prevent deformation of absorbent layers in the wet state, that is, to provide resilience to enable restoration of the absorbent layer when an external force such as compression and distortion is applied thereto, have been made. For example, an attempt has been made to form an absorbent layer by sandwiching a water absorbent resin between sheets comprising a synthetic fiber. Although this method can improve shape retention in the wet state to some degree, it causes a problem in that when the amount of the water absorbent resin is sufficiently large, the water absorbent resin sandwiched between the fiber sheets forms a gel layer after absorption, and the gel layer can be displaced by an extenal force to ruin the unity between the water absorbent resin gel/fiber substrate and cause leakage. Further, since synthetic fibers are not hydrophilic, a problem or deterioration of the permeability and the diffusibility of the liquid occurs.

Moreover, a proposal has been made to improve shape retention of the absorbent layer by mixing and dispersing water-absorbent resin in a fiber substrate which is a combination of a heat-adhesive synthetic fiber and fluff pulp with heat treatment. However, although this method provides improvement of shape retention, since the hydrophilic property of the absorbent layer deteriorates as the ratio of the synthetic fiber increases, a problem of deterioration of the liquid's permeability or diffusibility occurs as compared with a conventional absorbent layer consisting of cellulose fiber.

SUMMARY OF THE INVENTION

Accordingly, it is an object of the present invention to provide absorbent products that have excellent shape retention and unity of water-absorbent resin/fiber substrate even in a wet state, good liquid permeability and diffusibility without leakage and excellent surface dryness after absorption, and that can remain comfortable over a long period of use.

That is, the present invention provides an absorbent product comprising a liquid permeable surface sheet, a liquid nonpermeable back sheet and an absorbent layer located therebetween, wherein the absorbent layer comprises a water nonswellable synthetic fiber (a) or the synthetic fiber (a) and a cellulose fiber (b), and a water-absorbent resin (c). The weight ratio of (a):(b) is (100 to 20):(0 to 80) and the percentage content of (c) based on the weight sum of (a), (b) and (c) is 25 to 75 weight %. The absorbent layer is treated with a polyoxyalkylene-modified silicone surface active agent (d1). The present invention also provides an absorbent product comprising a liquid permeable surface sheet, a liquid nonpermeable back sheet and an absorbent layer located therebetween, wherein the absorbent layer comprises a water nonswellable synthetic fiber (a) or the synthetic fiber (a) and a cellulose fiber (b), and a water-absorbent resin (c). The weight ratio of (a):(b) is (100 to 20):(0 to 80) and the percentage content of (c) based on the weight sum of (a), (b) and (c) is 25 to 75 weight %. The absorbent layer is treated with a nonsilicone surface active agent having HLB of 8 to 14 (d2).

DETAILED DESCRIPTION OF THE INVENTION

Examples of water non-swellable synthetic fibers (a) in the present invention include thermoplastic fibers of polyolefin fibers such as polyethylene fibers, polypropylene fibers, polyethylene-polypropylene conjugate fibers; polyester fibers such as polyethylene terephthalate fibers, polyethylene terephthalate-polyethylene isophthalate copolymer conjugate fibers; polyolefin-polyester conjugate fibers, polyamide fibers and polyacrylonitrile fibers.

Among these examples of synthetic fibers, polyolefin fibers, polyester fibers and conjugate fibers thereof are preferable. Further, sheath & core type, eccentric core-sheath type and side-by-side type heat-adherent conjugate polyolefin fibers are preferable with respect to applicability to disposable diapers as having excellent shape retention property after liquid absorption.

The length and diameter of the above mentioned synthetic fibers are not particularly limited and in general, any one having a length of 1 to 200 mm and a diameter of 0.1 to 100 denier can be preferably used. Shape is not particularly limited and examples include web type, narrow cylinder type, cut split yarn type, staple fiber type and filament type.

Examples of cellulose fibers (b) optionally used include those used in conventional absorbent products such as fluff pulp and cotton type pulp. The materials, such as coniferous and deciduous tree, and production methods, such as chemical pulp, semichemical pulp, chemithermo mechanical pulp (CTMP) and bleaching method, are not particularly limited.

The weight ratio of (a):(b) is in general, (100 to 20) (0 to 80), preferably (100 to 25) (0 to 75), and more preferably (100 to 30):(0 to 70). If the amount of (a) is less than 20 weight %, shape retention of the absorbent layer deteriorates. Consequently, when an external force is applied to the absorbent layer by the user's movements at or after liquid absorption to compress or twist the absorbent layer, leakage or dryness deterioration would occur.

Examples of water-absorbent resins (c) of the present invention include crosslinked copolymers of starch-acrylic acid salt, crosslinked polyacrylic acid salt, self-crosslinked polyacrylic acid salt, saponified crosslinked copolymers of acrylate ester-vinyl acetate, crosslinked copolymers of isobutylene-maleic anhydride, crosslinked polysulfonic acid salt, derivatives of modified cellulose and crosslinked polyethylene oxide. Hydrophilic crosslinked polymers containing acrylic acid salt and/or acrylic acid as the main monomer component of the polymer are more preferable with respect to capability of absorbing and retaining large amounts of liquid by ion osmotic pressure, and unsusceptibility to liquid discharge even when a load or external force is applied. The kinds of these salts are not particularly limited, but in general, alkaline metal salts such as sodium and potassium are used.

Further, resins prepared by crosslinking the surface of a powdery water absorbent resin can be preferably used in the present invention. Unlike water-soluble resins, water-absorbent resins are water-insoluble and water-swellable.

Among the water-absorbent resins (c), those having an absorbency under a pressure-free state to physiological saline of 40 g/g or more, an absorbency under loading of 20 g/g or more and a gel elastic modulus of 20,000 dyne/cm$^2$ or more are preferable. Those having an absorbency under a pressure-free state of 45 to 75 g/g, an absorbency under loading of 25 to 50 g/g and a gel elastic modulus of 30,000 to 200,000 dyne/cm$^2$ are more preferable. Those having an absorbency under a pressure-free state of 50 to 75 g/g, an absorbency under loading of 35 to 50 g/g and a gel elastic modulus of 35,000 to 200,000 dyne/cm$^2$ are further preferable.

It is economical to use a water-absorbent resin having an absorbency under a pressure-free state of 40 g/g or more, since sufficient absorption property can be obtained with only a small amount of the water-absorbent resin. Further, it is economical to use a water-absorbent resin having an absorbency under loading of 20 g/g or more, since sufficient absorption property can be obtained with only a small amount of the water-absorbent resin. It is preferable to use a water-absorbent resin having a gel elastic modulus of 20,000 dyne/cm$^2$ or more, since the swelled gel after absorption does not become too soft, is not liable to be deformed by load or external force, and particles of the swelled gel are not liable to stick to each other to cause blocking or prevent permeation or diffusion of liquid.

Absorbency under pressure-free state, absorbency under loading and gel elastic modulus are measured by the following methods.

Absorbency under pressure-free state:

1 g of the water absorbent resin was placed in a 10 cm×20 cm size tea-bag prepared with 250-mesh nylon net and immersed in an excess amount of a physiological sodium chloride solution (concentration: 0.9 wt %) for 30 minutes. Then it was removed, drained of excess solution for 15 minutes, and measured for an increase of weight. The value was defined as water absorbency under pressure-free state.

Absorbency under loading:

In a cylindrical plastic tube (30 mm in inside diameter, 60 mm high) with a 250-mesh nylon net affixed on the bottom surface, 0.1 g of the water absorbent resin was placed and uniformly spread over the nylon net, on which a weight (30 mm in outside diameter) was placed so that a 20 g/cm$^2$ load was applied. A tube containing the water absorbent resin was immersed in a Petri dish (12 cm in diameter) containing 60 ml of the physiological sodium chloride solution, and left standing with the nylon net side down for 30 minutes. The 10-fold value of the increase in weight after 30 minutes of absorption was defined as water absorbency under loading.

Gel elastic modulus:

40 ml of artificial urine was added to 1 g of water-absorbent resin to form a 40 fold absorption gel. 0.1 g of the gel was placed in the center of the supporting table of a creep meter manufactured by YAMADEN Co., Ltd. Then a cylinder was lowered from the upper direction to compress the gel to 0.3 mm thickness. The stress (F) at the time of compression and the sectional area (S) of the compressed gel were measured to calculate the stress at the time of compression per a unit area by the following formula. And the value was designated as the gel elastic modulus.

Gel elastic modulus (dyne/cm$^2$)=(F×980)/S

The shape of a water absorbent resin (c) is not particularly limted and both powdery and fibrous forms can be used preferably. Preferable examples include powdery such as particle, granulate, agglomerate, lamellar, massive and spherical.

When the water absorbent resin is powdery, the average particle size is about 150 to 700 $\mu$m, preferably 200 to 600 $\mu$m, and more preferably 250 to 500 $\mu$m. Powders of a water-absorbent resin having an average particle size of 150 $\mu$m or more are preferable with respect to unsusceptibility of gel blocking in the case of contacting a liquid. It is further preferable with respect to the unsusceptibility the water absorbent resin from falling out of the absorbent layer. On the other hand, since the water absorption rate becomes drastically slow if the average particle size exceeds 700 $\mu$m, an average particle size of 700 $\mu$m or less is preferable. Further, since an average particle size of 700 $\mu$m or less does not provide an uncomfortable feel due to coarseness of the particles in the surface of a disposable diaper, nor the problem of breakage of the back sheet by coarse particles, it is preferable.

The ratio of water absorbent resin (c) in the present invention based on the sum of the weight of (a), (b) and (c) is 25 to 75 weight %, preferably 30 to 70 weight %, and more preferably 35 to 70 weight %.

If the ratio of (c) is less than 25 weight %, since a synthetic fiber (a) does not have a swellable property by water absorption, the abosrbent layer needs to be thick to secure a sufficient absorption capacity, and thus a thin product can not be provided. On the other hand, if the ratio of (c) exceeds 75 weight %, unity of the water absorbent resin and the fiber substrate can not be secured.

The amount of a water-absorbent resin (c) per one water-absorbent product is not particularly limited. For example, the amount for a disposable diaper is in general 5 to 20 g. The amount for a thin-type diaper is in general, 7 to 20 g, preferably 8 to 20 g. On the other hand, if the amount exceeds 20 g, a great amount of fiber substrate is required in order to secure the unity of the water absorbent resin and the fiber substrate, which is uneconomical. Unlike the above mentioned embodiment of disposable diapers, when an absorbent product is used for sanitary napkins or incontinence pads, the amount may be smaller according to the application and the size of the product.

In the present invention, polyoxyalkylene modified silicone surface active agents (d1) and/or nonsilicone surface active agent having HLB of 8 to 14 (d2) are used as a surface active agent. The term "surface active agent (d)" is used generically when both of them are referred to hereinafter.

Among the surface active agents (d), examples of polyoxyalkylene modified silicone surface active agents (d1) include polyoxyethylene modified dimethyl polysiloxane, dimethyl polysiloxane modified with block or random copolymers of polyoxyethylene-polyoxypropylene, dimethylpolysiloxane modified by polyoxyethylene having an end alkyl group of 1 to 12 carbon atoms, dimethylpolysiloxane modified with block or random copolymers of polyoxyethylene-polyoxypropylene having an end alkyl group of 1 to 12 carbon atoms, and dimethyl polysiloxane derivatives which are dimethyl polysiloxane having an amino group or an epoxy group at the end and/or in the molecule modified with the above mentioned polyoxyalkylene. Among these examples, polyoxyethylene modified dimethyl polysiloxane and dimethylpolysiloxane modified with block or random copolymers of polyoxyethylene-polyoxypropylene are preferable, and polyoxyethylene modified dimethyl polysiloxane is further preferable with respect to the availability at a low price.

The molecular weight of polyoxyalkylene-modified silicone surface active agents (d1) is not particularly limited, and in general, is 500 to 10,000, preferably 500 to 5,000, and more preferably 500 to 3,000. If the molecular weight is 500 or more, since the treatment with a great amount of (d) is not required in order to achieve good permeability and diffusibility of a liquid in the absorbent layer, it is economical. Further, if the molecular weight is 10,000 or less, since the viscosity would not be too high, a uniform treatment can be facilitated. Accordingly, since an extremely great amount of solvent is not required in order to adjust (d1) to an appropriate viscosity and thus the process of eliminating the solvent is not particularly required, it is efficient.

The percentage content of a polyoxyethylene group of a polyoxyalkylene-modified silicone surface active agent (d1) can vary according to the degree of desired water affinity, and in general it is 25 to 75 weight %, preferably 30 to 70 weight %, and more preferably 40 to 60 weight % The ratio of an oxyethylene group and an oxypropylene group is not particularly limited as long as the percentage content of a polyoxyethylene group is in the above mentioned range, and in general is (100 to 50):(0 to 50), preferably (100 to 60) (0 to 40). It is preferable that the percentage content of a polyoxyethylene group is 25 weight % or more, since the water affinity would not deteriorate, and a good permeability and diffusibility of a liquid are secured in treating the absorbent layer. Further, it is preferable that the percentage content of a polyoxyethylene group is 75 weight % or less, since the water solubility would not become too strong and the permeability and diffusibility of a liquid in repetitive absorptions can be maintained.

Examples of nonsilicone surface active agents having HLB of 8 to 14 (d2) include ethyleneoxide adducts of higher alcohols such as polyoxyethylene oleylether, polyoxyethylene cetylether and polyoxyethylene laurylether; ethylene oxide adducts of alkylphenol such as polyethylene nonylphenylether; polyoxyethylene monoaliphatic acid esters such as polyoxyethylene monooleate, polyoxyethylene monostearate and polyoxyethylene monolaurate; polyethylene glycol dialiphatic acid esters such as polyoxyethylene dioleate, polyoxyethylene distearate and polyoxyethylene dilaurate; ethylene oxide adducts of partial esters of polyhydric alcohol with aliphatic acid such as sorbitan monooleate (EO 5 mole), sorbitan monostearate (EO 4 mole), sorbitan monolaurate (EO 4 mole) and sorbitan monolaurate. (Herein "EO" denotes ethylene oxide and a number in the parentheses is an adduct mole number.) These can be used as a mixture. Among these examples of the nonsilicone surface active agents, nonsilicone surface active agents having HLB of 9 to 13 are preferable. HLB (Hydrophile-Lipophile Balance) describes the balance of the water affinity and the oil affinity of a surface active agent. HLB can be controlled by the adduct mole number of ethylene oxide or the molecular weight of polyethylene glycol. Surface active agents (d) can be selected from (d1) and/or (d2), that is, both (d1) and (d2) can be used at the same time.

The amount of surface active agents (d) used for treatment can vary according to the ratio of (a) and (b), the kind of (a) and the absorption property of (c), and in general is 0.01 to 5 weight %, preferably 0.02 to 2 weight %, and more preferably 0.03 to 1 weight %. It is preferable to have the amount for treatment of 0.01 weight % or more since an excellent improvement of permeability and diffusibility of a liquid can be achieved. On the other hand, it is uneconomical to have the treament with the amount over 5 weight % since it does not further improve the property compared with the treatment conducted within the range of 0.01 to 5 weight %. Therefore 5 weight % or less is preferable. The amount of 5 weight % or less is preferable since stickiness is not generated.

Examples of methods of obtaining an absorbent layer by applying water absorbent resin (c) to fiber substrate comprising a synthetic fiber (a) and a cellulose fiber (b) optionally used include (1) a method of mixing (a), (b) and (c) simultaneously, (2) a method of mixing the mixture of (a) and (b) into (c), (3) a method of mixing the mixture of (b) and (c) to (a), (4) a method of mixing the mixture of (a ) and (c) into (b), (5) a method of mixing (b) and (c) separately into (a) and (6) a method of laminating a mixture of (a) and (b) and then sprinkling (c) thereon followed by laminating a mixture of (a) and (b) to form a sandwiched structure. In these methods, (b) is an optional component used as needed. Among these examples, methods (1), (2) and (6) are preferable. The apparatus used in these methods is not particularly limited and a common apparatus can be used.

An absorbent layer formed accordingly is subjected to heat treatment to be finished as an absorbent layer having an excellent shape retention property in the wet state. A method of heat treatment is not particularly limited and examples include a method of treating with hot-air, a method of passing through a heat roll and a method of irradiating infrared ray. Temperature and duration of heat treatment can be optionally selected as long as (a) can adhere to each other according to the kind of (a), the amount of (a) and the production speeed of disposable diapers. The temperature of the heat treatment is, in general, 80 to 250° C. preferably 90 to 200° C., and more preferably 100 to 180° C. By having the temperature of heat treatment of 80° C. or more, since the heating time need not be long, sufficient heating treatment can be conducted without the need of a large heating apparatus, and thus it is economical. Further, it is preferable since the production speed of absorbent products is not lowered. Further, it is preferable to have the temperature of heat treatment of 250° C. or less, since heat deterioration of (b) or (c) is not caused.

The heating duration can be optionally selected as long as (a) can adhere to each other according to the kind of (a), the amount of (a) and the production speed of the absorbent product. With respect to adhesion and production speed of absorbent products, the heating duration is, in general, 0.5 second to 3 minutes, preferably 1 second to 1 minute.

Treatment of the absorbent layer with the surface activate agents (d) in this invention can be conducted by any suitable method as long as the uniform application is secured. In general, an absorbent layer is treated with diluted solution of a surface active agent of approximately 1 to 10 weight % concentration. By having the treatment with (d) after forming the absorbent layer, since the surface active agent (d) can be uniformly treated to (a), (b) and (c), an excellent permeability and diffusibiliy of a liquid can be secured. If a synthetic fiber pretreated by (d) is used as (a), a sufficient effect can not be achieved.

This treatment can be conducted either at a stage before the heat treatment of the absorbent layer or a stage after the heat treatment. When this treatment is conducted after the heat treatment, in general, it is followed by the drying process. When this treatment is conducted before the heat treatment, the drying process is unnecessary.

The method and the apparatus for treating the absorbent layer with (d) are not particularly limited. Examples include a method of soaking the absorbent layer in a solution of (d) and optionally followed by squeezing with a mangle, a method of spraying the absorbent layer with a solution of (d) and a method of treating the absorbent layer with an oiling roll having a solution of (d) thereon.

Other compounds can be included in a solution of the above mentioned surface active agents (d) of the present invention as long as the effects of the present invention are not disturbed. Examples of such compounds include antistatic agents such as alkyl phosphate type anion surface active agent and quaternary ammonium salt type or alkyl imidazolinium salt type cationic surface active agents, emulsifiers, smoothing agents, converging agents such as other nonionic surface active agents and other modified silicone surface active agents, antiseptics, perfumes and deodorants.

Absorbent layers treated with a surface active agent (d) accordingly can form a single layer or a plurality of layers with optional layers of a water-absorbent paper or a pulp, and finished as an absorbent product provided with a liquid permeable surface sheet or a nonwoven fabric in the surface and a liquid nonpermeable back sheet in the rear side, and further with gathers and application tapes for fixation. Materials and kinds of the liquid permeable surface sheets, liquid nonpermeable back sheets, gathers and application tapes, production methods of absorbent products are not particularly limited and materials, kinds, and production methods used in conventional absorbent products can be applied.

Although it depends on the desired finished products, examples of a liquid permeable surface sheet used in the present invention include mesh-type sheets comprising polyethylene, polypropylene or polytetrafluoroethylene, and sheets having holes with a several 100 micron diameter comprising polyethylene, polypropylene or polytetrafluoroethylene. Among these examples, a mesh type polypropylene sheet is preferable.

Although it depends on the desired finished products, examples of a liquid nonpermeable back sheet used in the present invention include polyethylene sheets, polypropylene sheets, polytetrafluoroethylene sheets, stretched polyethylene sheets, stretched polypropylene sheets provided with air ventilation by stretching and stretched polytelytetrafluoroethylene sheets provided with air ventilation by stretching. Among these examples, stretched drawn polypropylene or polyethylene sheets with air ventilation are preferable.

The present invention will be further illustrated with reference to the Examples and Comparative Examples. However, this invention is not limited to these embodiments. Embodiments of disposable diapers will be explained in Examples and Comparative Examples hereinafter, but this invention is not limited to disposable diapers as the absorbent products. But the present invention can be applied to embodiments of other absorbent products such as sanitary napkins and incontinence pads. Absorption rate, diffusion area, surface dryness and shape retention property are evaluated in the below mentioned methods. "%" denotes weight % hereinafter unless otherwise specified.

Absorption rate: An acryl plate having the size same as a disposable diaper having the weight of 0.5 kg with a cylinder having a bore of 3 cm in the center is located on the disposable diaper and a 4.5 kg load is applied on the acryl plate to provide a total load of 5 kg. The acryl plate is provided with a hole in the center to discharge a liquid from the above mentioned cylinder. 80 ml of artificial urine colored with a blue ink is poured in the cylinder to have the disposable diaper absorb it. After 30 minutes, a further 80 ml of artificial urine is poured for the second time. After 30 minutes, a further 80 ml of artificial urine is poured similarly for the third time and the absorption time is measured to be determined as the absorption rate.

Diffusion area

After the third pour of the artificial urine and measuring the absorption rate, the area in which the artificial urine is absorbed and expanded, which is colored to be blue, is measured and determined as the diffusion area.

Surface dryness

After measuring the diffusion area, the surface dryness of disposable diapers in the area where the artificial urine is poured is judged by touching by 10 panelists and evaluated according to the below mentioned four grades. The average of the evaluation is determined as the surface dryness.

⊚: Good dryness

○: Satisfactory dryness although slightly moist

Δ: Moist state with a little dryness

×: Wet state without dryness

Shape retention property: After 30 minutes from the third pour of the artificial urine, the disposable diaper is twisted by hand and the shape retention property after 5 minutes is evaluated by visual observation and evaluated according to the below mentioned three grades.

⊚: Restored the original shape

○: Almost restored the original shape satisfactorily

×: The shape is destroyed

Absorbent layer (A)

A mixture prepared by mixing 30 weight parts of a sheath & core type conjugate fiber having polypropylene as the core component and polyethylene as the sheath component ("ES Fiber EAC" produced by Chisso Corporation; melting point of the low-melting point component: 110° C.), 70 weight parts of fluff pulp and 50 weight parts of crosslinked sodium acrylate-based water absorbent resin (absorbency under pressure-free state: 50 g/g, absorbency under loading: 28 g/g, gel elastic modulus: 92,000 dyne/cm$^2$, average particle size 480 μm) in an air blender was uniformly laminated to have a weight of approximately 400 g/m$^2$ and pressed for 90 seconds with 5 kg/cm$^2$ pressure. Then the absorbent layer was cut in a 14 cm×36 cm rectangular shape and sprayed with 10 parts of 1% aqueous solution of polyoxyethylene modified dimethylpolysiloxane ("SANSILICON M-84" manufactured by Sanyo Chemical Industries, Ltd., containing approximately 50% by weight of polyoxyethylene groups and having an average molecular weight of approximately 1,000,), followed by hot air treatment at 130° C. for 3 minutes to obtain the absorbent layer (A) of the present invention.

Absorbent layers (B) and (C)

Except that the ratio (weight ratio) of the conjugate fiber, the fluff pulp and the water absorbent resin was changed as mentioned below, the absorbent layer (B) and the absorbent layer (C) were obtained by the same procedure as the absorbent layer (A).

Absorbent layer (B) conjugate fiber/fluff pulp/absorbent resin=50/50/70

Absorbent layer (C) conjugate fiber/fluff pulp/absorbent resin=100/0/100

Absorbent layer (D)

Except that 25 weight parts of the 1% aqueous solution of polyoxyethylene modified dimethyl polysiloxane was sprayed instead of 10 weight parts in the absorbent layer (A), the absorbent layer (D) was obtained by the same procedure as the absorbent layer (A).

Absorbent layers (E) and (F)

Except that random copolymers of polyoxyethylene-polyoxypropylene (copolymerization mole ratio oxyethylene/oxypropylene=75/25) modified dimesyl polysiloxane (average molecular weight: approximately 2,500, percentage content of polyoxyethylene group: approximately 40%) was used instead of polyoxyethylene modified dimethyl polysiloxane in the absorbent layers (A) and (D), the absorbent layer (E) and the absorbent layer (F) were obtained by the same procedure as the absorbent layers (A) and (D) respectively.

Absorbent layer (G)

Except that the same amount of an eccentric core-sheath type conjugate fiber having polypropylene as the core component and polyethylene as the sheath component ("ES Fiber EA" produced by Chisso Corporation; melting point of the low-melting point component: 110° C.) was used instead of the sheath & core type conjugate fiber ("ES Fiber EAC" produced by Chisso Corporation; melting point of the low-melting point component: 110° C.), the absorbent layer (G) was obtained by the same procedure as the absorbent layer (A).

Absorbent layer (H)

Except that the same amount of surface crosslinked starch-sodium acrylate copolymers-based water absorbent resin particles (absorbency under pressure-free state 58 g/g, absorbency under loading: 36 g/g, gel elastic modulus: 105,000 dyne/cm$^2$, average particle size: 350 μm) was used instead of the crosslinked sodium polyacrylate-based water absorbent resin (absorbency under pressure-free state: 50 g/g, absorbency under load: 28 g/g, gel elastic modulus: 92,000 dyne/cm$^2$, average particle size: 480 μm), the absorbent layer (H) was obtained by the same procedure as the absorbent layer (A).

Comparative absorbent layer (f)

Except that polyoxyethylene modified dimethyl polysiloxane was not sprayed on the absorbent layer, the comparative absorbent layer (f) was obtained by the same procedure as the absorbent layer (A).

Comparative absorbent layer (g)

Except that the weight ratio of conjugate fiber/fluff pulp/water absorbent resin=30/70/50 in the comparative absorbent layer (f) was changed to the weight ratio of conjugate fiber/fluff pulp/water absorbent resin=100/0/100, the comparative absorbent layer (g) was obtained by the same procedure as the comparative absorbent layer (f).

Comparative absorbent layers (h) to (j)

Except that the weight ratio of conjugate fiber/fluff pulp/water absorbent resin=30/70/50 in the absorbent layer (A) of the present invention was changed to the below mentioned weight ratio of conjugate fiber/fluff pulp/absorbent resin, the comparative absorbent layers (h) to (j) were obtained by the same procedure as the absorbent layer (A).

Comparative absorbent layer (h): conjugate fiber/fluff pulp/absorbent resin=0/100/50

Comparative absorbent layer (i): conjugate fiber/fluff pulp/absorbent resin=10/90/50

Comparative absorbent layer (j): conjugate fiber/fluff pulp/absorbent resin=50/50/350

Comparative absorbent layer (k)

Except that polyoxyethylene modified dimesyl polysiloxane (average molecular weight: approximately 1,000, percentage content of polyoxyethylene group: approximately 20%) was used instead of polyoxyethylene modified dimethyl polysiloxane in the absorbent layer (A) in the present invention, the comparative absorbent layer (k) was obtained by the same procedure as the absorbent layer (A).

Examples 1 to 8

Model disposable diapers were prepared by cutting the absorbent layers (A) to (H) of the present invention in a 14 cm×36 cm rectangular shape respectively, applying water absorbent paper having the same size as the absorbent layer to both sides of the absorbent layer and locating a polyethylene sheet commonly used in disposable diapers on the rear side and a nonwoven fabric on the surface side. Evaluation results of these model disposable diapers in terms of absorption rate, diffusion area, surface dryness and shape retention property are described in Table 1.

Comparative Examples 1 to 6

Comparative model disposable diapers were prepared with the comparative absorbent layers (f) to (k) by the same process as the Examples. Evaluation results of these model disposable diapers in terms of absorption rate, diffusion area, surface dryness and shape retention property are described in Table 1.

TABLE 1

|         |   | absorption rate (second) | diffusion area (cm$^2$) | surface dryness | shape retention property |
|---------|---|--------------------------|-------------------------|-----------------|--------------------------|
| Example | 1 | 83                       | 297                     | ◉               | ○                        |
|         | 2 | 84                       | 283                     | ◉               | ◉                        |

TABLE 1-continued

|  |  | absorption rate (second) | diffusion area (cm²) | surface dryness | shape retention property |
|---|---|---|---|---|---|
|  | 3 | 88 | 275 | ⊚ | ⊚ |
|  | 4 | 49 | 310 | ⊚ | ○ |
|  | 5 | 85 | 288 | ⊚ | ○ |
|  | 6 | 53 | 303 | ⊚ | ○ |
|  | 7 | 80 | 292 | ⊚ | ○ |
|  | 8 | 77 | 292 | ⊚ | ○ |
| Comparative Example | 1 | 170 | 185 | x | ○ |
|  | 2 | 224 | 175 | x | ⊚ |
|  | 3 | 61 | 285 | ○ | x |
|  | 4 | 77 | 281 | ○ | x |
|  | 5 | 280 | 186 | ○ | x |
|  | 6 | 156 | 198 | Δ | ○ |

Absorbent layer (I)

A mixture prepared by mixing 30 weight parts of a sheath & core type conjugate fiber having polypropylene as the core component and polyethylene as the sheath component ("ES Fiber EAC" produced by Chisso Corporation; melting point of the low-melting point component: 110° C.), 70 weight parts of fluff pulp and 50 weight parts of crosslinked sodium acrylate-based water absorbent resin (absorbency under pressure-free state: 50 g/g, absorbency under loading: 28 g/g, gel elastic modulus: 92,000 dyne/cm², average particle size 480 μm) in an air blender was uniformly laminated to have a weight of approximately 400 g/m² and pressed for 90 seconds with 5 kg/cm pressure. Then the absorbent layer was cut in a 14 cm×36 cm rectangular shape and sprayed with 10 parts of 1% aqueous solution of a nonionic surface active agent, polyoxyethylene oleyl-cetyl ether ("Emulmin 60" manufactured by Sanyo Chemical Industries, Ltd. ; HLB 10.3), followed by hot air treatment at 130° C. for 3 minutes to obtain the absorbent layer (I) of the present invention.

Absorbent layers (J) and (K)

Except that the ratio (weight ratio) of the conjugate fiber, the fluff pulp and the water absorbent resin was changed as mentioned below, the absorbent layer (J) and the absorbent layer (K) were obtained by the same procedure as the absorbent layer (I).

Absorbent layer (J): conjugate fiber/fluff pulp/absorbent resin=50/50/70

Absorbent layer (K): conjugate fiber/fluff pulp/absorbent resin=100/0/100

Absorbent layer (L)

Except that 25 weight parts of the 1% aqueous solution of polyoxyethylene oleyl-cetyl ether was sprayed instead of 10 weight parts in the absorbent layer (I), the absorbent layer (L) was obtained by the same procedure as the absorbent layer (I).

Absorbent layers (M) to (P)

Except that the below mentioned surface active agents were used instead of polyoxyethylene oleyl-cetyl ether in the absorbent layer (I), the absorbent layers (M) to (P) were obtained by the same procedure as the absorbent layer (I).

Absorbent layer (M): polyoxyethylene oleyl-cetyl ether (a nonionic surface active agent "Emulmin 40" produced by Sanyo Chemical Industries, Ltd. ; HLB 8.0)

Absorbent layer (N): polyoxyethylene nonylphenyl ether (a nonionic surface active agent "Nonipol 40" produced by Sanyo Chemical Industries, Ltd. ; HLB 8.9)

Absorbent layer (O): sorbitan monolaurate-EO 4 mole (HLB 8.6)

Absorbent layer (P) polyoxyethylene lauryl-myristyl ether (a nonionic surface active agent "Nonipol Soft SS-50" produced by Sanyo Chemical Industries, Ltd.; HLB 10.6)

Absorbent layer (Q)

Except that the same amount of an eccentric core-sheath type conjugate fiber having polypropylene as the core component and polyethylene as the sheath component ("ES Fiber EA" produced by Chisso Corporation; melting point of the low-melting point component: 110° C.) was used instead of the sheath & core type conjugate fiber ("ES Fiber EAC" produced by Chisso Corporation; melting point of the low-melting point component: 110° C.), the absorbent layer (Q) was obtained in the same procedure as the absorbent layer (I).

Absorbent layer (R)

Except that the same amount of surface crosslinked starch-sodium acrylate copolymers-based water absorbent resin particles (absorbency under pressure-free state 58 g/g, absorbency under loading 36 g/g, gel elastic modulus: 105,000 dyne/cm², average particle size: 350 μm) was used instead of the crosslinked sodium polyacrylate-based water absorbent resin (absorbency under pressure-free state: 50 g/g, absorbency under load: 28 g/g, gel elastic modulus: 92,000 dyne/cm², average particle size: 480 μm), the absorbent layer (R) was obtained by the same procedure as the absorbent layer (I).

Comparative absorbent layer (m)

Except that polyoxyethylene oleyl-cetyl ether was not sprayed on the absorbent layer, the comparative absorbent layer (m) was obtained by the same procedure as the absorbent layer (I).

Comparative absorbent layer (n)

Except that the weight ratio of conjugate fiber/fluff pulp/water absorbent resin=30/70/50 in the comparative absorbent layer (m) was changed to the weight ratio of conjugate fiber/fluff pulp/water absorbent resin=100/0/100, the comparative absorbent layer (n) was obtained by the same procedure as the comparative absorbent layer (m).

Comparative absorbent layers (o) to (q)

Except that the weight ratio of conjugate fiber/fluff pulp/water absorbent resin=30/70/50 in the absorbent layer (I) of the present invention was changed to the below mentioned weight ratio of conjugate fiber/fluff pulp/absorbent resin, the comparative absorbent layers (o) to (q) were obtained by the same procedure as the absorbent layer (I).

Comparative absorbent layer (o): conjugate fiber/fluff pulp/absorbent resin=0/100/50

Comparative absorbent layer (p): conjugate fiber/fluff pulp/absorbent resin=10/90/50

Comparative absorbent layer (q): conjugate fiber/fluff pulp/absorbent resin=50/50/350

Comparative absorbent layers (r) and (s)

Except that surface active agents having the below mentioned HLBs were used instead of polyoxyethylene oleyl-cetyl ether having HLB 10.3 of the absorbent layer (I) of the present invention, the comparative absorbent layers (r) and (s) were obtained by the same procedure as the absorbent layer (I).

Comparative absorbent layer (r): polyoxyethylene non-ylphenyl ether (a nonionic surface active agent "Nonipol 20" produced by Sanyo Chemical Industries, Ltd.; HLB 5.7)

Comparative absorbent layer (s): polyoxyethylene non-ylphenyl ether (a nonionic surface active agent "Nonipol 120" produced by Sanyo Chemical Industries, Ltd.; HLB 14.8)

Examples 9 to 18

Model disposable diapers were prepared by cutting the absorbent layers (I) to (R) of the present invention in a 14 cm×36 cm rectangular shape respectively, applying water absorbent paper having the same size as the absorbent layer to both sides of the absorbent layer and locating a polyethylene sheet commonly used in disposable diapers on the rear side and a nonwoven fabric on the surface side. Evaluation results of these model disposable diapers in terms of absorption rate, diffusion area, surface dryness and shape retention property are described in Table 2.

Comparative Examples 7 to 13

Comparative model disposable diapers were prepared with the comparative absorbent layers (m) to (s) by the same process as Examples. Evaluation results of these model disposable diapers in terms of absorption rate, diffusion area, surface dryness and shape retention property are described in Table 2.

TABLE 2

|  |  | absorption rate (second) | diffusion area (cm$^2$) | surface dryness | shape retention property |
|---|---|---|---|---|---|
| Example | 9 | 83 | 277 | ⊙ | ○ |
|  | 10 | 78 | 271 | ⊙ | ⊙ |
|  | 11 | 80 | 264 | ⊙ | ⊙ |
|  | 12 | 66 | 294 | ⊙ | ○ |
|  | 13 | 108 | 259 | ⊙ | ○ |
|  | 14 | 97 | 262 | ⊙ | ○ |
|  | 15 | 90 | 258 | ⊙ | ○ |
|  | 16 | 84 | 270 | ⊙ | ○ |
|  | 17 | 85 | 280 | ⊙ | ○ |
|  | 18 | 82 | 268 | ⊙ | ○ |
| Comparative | 7 | 170 | 185 | x | ○ |
| Example | 8 | 231 | 177 | x | ⊙ |
|  | 9 | 64 | 280 | ○ | x |
|  | 10 | 71 | 268 | ○ | x |
|  | 11 | 220 | 182 | ○ | x |
|  | 12 | 153 | 195 | Δ | ○ |
|  | 13 | 260 | 191 | x | ○ |

Absorbent products of the present invention have the following characteristics and advantageous effects. ①̂ Excellent absorption property and absorption rate even in the case of repetitive absorptions. ②̂ Good liquid diffusion to provide excellent surface dryness after absorption. ③̂ Reduced leakage of the absorbed liquid. ④̂ Excellent shape retention property to external force such as shearing, compression and wrinkle by the wearer's movement in the moist condition. ⑤̂ Excellent unity of the absorbent resin and the fiber substrate Since the absorbent products of the present invention have the above mentioned effects, they are preferable for the application in disposable diapers (disposable diapers for infants or for adults), and in particular, in thin-type disposable diapers that have a large ratio of the water absorbent resin/fiber material.

Further, the absorbent products of the present invention are preferable for the application in other hygienic materials such as sanitary napkins, incontinence pads, mother's milk pads, underpads for medical operations, childbirth mats, dressing materials for injury protection, and pet sheets as well as various kinds of absorbent sheets such as freshness retaining sheets, drip absorbent sheets, anti-dewing sheets, paddy seedling sheets, concrete curing sheets, oil/water separating sheets and fire extinction sheets.

What is claimed is:

1. An absorbent product comprising a liquid permeable surface sheet, a liquid nonpermeable back sheet and an absorbent layer located therebetween, wherein the absorbent layer comprises a water nonswellable synthetic fiber (a) or the combination of the synthetic fiber (a) and a cellulose fiber (b), and a water-absorbent resin (c) that is capable of absorbing 45 to 75 times its weight of physiological saline under a pressure free state, and is capable of absorbing 25 to 50 times its weight of physiological saline under loading and has a gel elastic modulus of 30,000 to 200,000 dyne/cm$^2$, with the weight ratio of the synthetic fiber: the cellulose fiber being (100 to 20):(0 to 80) and the percentage content of the water-absorbent resin based on the weight sum of the synthetic fiber, the cellulose fiber and the water-absorbent resin is 25 to 75% by weight, the absorbent layer having applied thereto an ethylene oxide added moiety- or polyethylene glycol moiety-containing nonsilicone surface active agent having HLB of 8 to 14 (d2), whereby the permeability and diffusibility of absorbed liquid are improved.

2. The absorbent product according to claim 1, wherein the synthetic fiber (a) is at least one selected from a group consisting of polyolefin fibers, polyester fibers and a conjugate fiber thereof.

3. The absorbent product according to claim 1, wherein the absorbent resin (c) is a powdery hydrophilic crosslinked polymer derived from acrylic acid salt and/or acrylic acid as a main monomer component for the polymer.

4. The absorbent product according to claim 1, wherein the amount of the nonsilicone surface active agent having HLB of 8 to 14 (d2) used for treatment is 0.01 to 5% by weight based on the weight sum of (a), (b) and (c).

5. The absorbent product according to claim 1, wherein the nonsilicone surface active agent (d2) has HLB of 9 to 13.

6. The absorbent product according to claim 1, wherein said nonsilicone surface active agent having HLB of 8 to 14 (d2) is at least one selected from the group consisting of ethylene oxide adducts of higher alcohol, ethylene oxide adducts of alkyl phenol, polyoxyethylene monoaliphatic acid ester, polyethylene glycol dialiphatic acid ester, and ethylene oxide adducts of partial ester of polyhydric alcohol with aliphatic acid.

* * * * *